(12) United States Patent
Swilling

(10) Patent No.: US 7,927,633 B2
(45) Date of Patent: Apr. 19, 2011

(54) ADAPTOGENIC TEA

(76) Inventor: Janiece Diane Swilling, San Diego, CA (US)

( * ) Notice: Subject to any disclaimer, the term of this patent is extended or adjusted under 35 U.S.C. 154(b) by 287 days.

(21) Appl. No.: 12/057,614

(22) Filed: Mar. 28, 2008

(65) Prior Publication Data

US 2009/0246300 A1  Oct. 1, 2009

(51) Int. Cl.
*A61K 36/00* (2006.01)
*A61K 36/79* (2006.01)
*A61K 36/38* (2006.01)
*A61K 36/481* (2006.01)
*A61K 36/76* (2006.01)
*A61K 36/54* (2006.01)
*A61K 31/685* (2006.01)
*A61K 36/82* (2006.01)
*A61K 36/48* (2006.01)
*A61K 36/889* (2006.01)

(52) U.S. Cl. ........ 424/725; 424/729; 424/757; 424/739; 424/727

(58) Field of Classification Search .................. None
See application file for complete search history.

(56) References Cited

U.S. PATENT DOCUMENTS 5,567,424 A * 10/1996 Hastings .................. 424/195.17
2008/0199586 A1 * 8/2008 Barton ........................ 426/599

FOREIGN PATENT DOCUMENTS

WO   WO 2004056382 A1 * 7/2004

OTHER PUBLICATIONS

Berenbaum, Synergy, additivism and antagonism in immunosuppression, Clin Exp Immuno128: 1-18, 1977.*

* cited by examiner

*Primary Examiner* — Qiuwen Mi

(57) ABSTRACT

A natural adaptogenic tea is prepared from adaptogens to counter adverse physical, chemical, or biological stressors and to promote t-cell activity and k-cell activity. Also, the composition is high in antioxidants and discourages free radicals. Moreover, the composition improves liver performance, resulting in improved toxin removal and improved nutrient absorption. In addition to these benefits, the composition improves capillary dilation, thereby providing better oxygenation to the brain. The tea is prepared from adaptogens including rhodiola, ashwagandha, schizandra berry, eleuthero and astralagus. Also, the tea includes damiana leaf, passion flower, milk thistle, white willow bark, goji berry, mangosteen, pomegranate, green tea, and sarsaparilla.

18 Claims, No Drawings

ADAPTOGENIC TEA

FIELD OF THE INVENTION

The present invention pertains generally to compositions for human consumption to promote health. More particularly, the present invention pertains to teas containing adaptogenic botanicals. The present invention is particularly, but not exclusively, useful as a natural tea for providing energy, promoting stress resistance, promoting t-cell activity, promoting k-cell activity, and discouraging free radicals.

BACKGROUND OF THE INVENTION

As general nutritional awareness increases, there is a corresponding increase in demand for healthy beverages. For instance, it is now known that drinks relying on sugar to provide energy result instead in lethargy. Further, it is known that certain energy drinks may provide a short-term boost in energy while having long-term negative effects. For example, many of these drinks rely on stimulants such as added caffeine or ephedra to boost a drinker's energy level.

In addition to providing energy, a nutritional beverage should promote health. For instance, certain drinks, such as teas, may aid in soothing anxiety or relieving depression. Other teas may promote restful sleep or attentiveness. Still others may enhance performance of specific organs, such as the heart, brain, kidneys, liver, lungs, etc.

While there may be known drinks which provide benefits in certain areas, there exists a need for a drink that promotes overall health while supporting various biological processes. Further, such a tea must avoid adverse drug interactions resulting from its diverse components.

In light of the above, it is an object of the present invention to provide a composition for brewing a natural tea to improve a drinker's health. Another object of the present invention is to provide a tea that counters adverse physical, chemical, or biological stressors. Still another object of the present invention is to provide a composition that promotes t-cell activity and k-cell activity. Still another object of the present invention is to provide an adaptogenic tea brewed from at least five distinct adaptogens. Yet another object of the present invention is to provide an adaptogenic tea for promoting health that is easy to prepare and comparatively cost effective.

SUMMARY OF THE INVENTION

In accordance with the present invention, a composition for brewing a natural tea is provided to improve a drinker's health. Specifically, upon ingestion, the composition counters adverse physical, chemical, or biological stressors. Further, the composition promotes t-cell activity and k-cell activity. Also, the composition is high in antioxidants and discourages free radicals. Moreover, the composition improves liver performance, resulting in improved toxin removal and improved nutrient absorption. In addition to these benefits, the composition improves capillary dilation, thereby providing better oxygenation to the brain. Also, this composition contains non-steroidal anabolic properties that allow the drinker to exercise harder, work out longer, build muscle more efficiently and recover more rapidly from the stress of working out and competing.

Importantly, the composition comprises adaptogenic botanicals. The accepted functional definition of adaptogens requires that the substance (a) be nontoxic to the recipient in normal doses; (b) produce a nonspecific response in the body, an increase in the power of resistance against multiple stressors including physical, chemical, or biological agents, and (c) have a normalizing influence on physiology, irrespective of the direction of change from physiological norms caused by the stressor. Generally, adaptogens increase the body's resistance to stresses such as trauma, anxiety and bodily fatigue. As such, adaptogens constitute a new class of natural, homeostatic metabolic regulators.

It has been reported that adaptogens uniquely balance endocrine hormones and the immune system. Further adaptogens may help the body to maintain optimal homeostasis. In any case, adaptogens have a normalizing effect on the body and are capable of either toning down the activity of hyperfunctioning systems or strengthening the activity of hypofunctioning systems. However, adaptogens are also functional at the level of allostasis which is a more dynamic reaction to long term stress, lacking the fixed reference points of homeostasis.

While adaptogenic botanicals have a diffuse effect, it has been determined that they typically comprise triterpenes including triterpenoid saponins: dammarane triterpene saponins, cucurbitacins; phytosterols: beta-sitosterol; and phytoecdysteroids: 20-ecdysone, turkesterone; phenylpropanes including flavonoids: glucopyranosides, prenylated flavonoids, flavan glycosides; lignans: schizandrin, sesamin, syringaresinol; and oxylipins including hydroxylated fatty acids: octadecadienoic acid. In addition to the above constituents, many adaptogens contain polysaccharides that have been reported to stimulate immune system components and have immune system enhancing benefits. Polysaccharide-rich plants have a long history of use in traditional practices. In addition to stimulating the immune system, they are used to increase vital energy.

DESCRIPTION OF THE PREFERRED EMBODIMENTS

In the present invention, the synergistic composition includes adaptogens such as rhodiola, ashwagandha, schizandra berry, and eleuthero. Further, the composition includes goji berry and astragalus, both of which may be determined to be adaptogens. In addition to the adaptogens, the composition includes sarsaparilla, mangosteen, pomegranate fruit, damiana leaf, passion flower, green tea, milk thistle, and white willow bark.

Specifically, the composition is prepared with two cups each of rhodiola, ashwagandha, schizandra berry, sarsaparilla, and goji berry. Further, the composition includes one cup each of mangosteen, pomegranate fruit, damiana leaf, passion flower, eleuthero, green tea, astragalus, milk thistle, and white willow bark. With these ingredients, nineteen cups of the composition are prepared. Preferably, each of the ingredients is provided in a powdered form. The ingredients are then brewed in boiling water for 3-5 minutes. The resulting adaptogenic tea may be drunk straight, or with cinnamon, sugar, milk or soy milk. Further, fruit and hibiscus flower can be added to the tea and frozen to create a frozen pop. Another frozen version of the composition can be formed by adding soy milk, vanilla, cinnamon, virgin coconut oil and lecithin before freezing.

In the composition, adaptogenic rhodiola (*Rhodiola Rosea*) is effective for improving mood, for alleviating depression, and for otherwise improving mental performance. Further, rhodiola has been shown to improve physical performance, reduce fatigue, and prevent high-altitude sickness. These effects are attributed to the ability of rhodiola to optimize serotonin and dopamine levels, due to monoamine oxidase inhibition and to its influence on opioid peptides such as beta-endorphins.

Further, the adaptogen ashwagandha (*Withania Somnifera*) is utilized in the composition to work on a nonspecific basis to increase health and longevity. Traditionally, ashwagandha has been used as an aphrodisiac, as a diuretic and for treating memory loss. In modern times, the herb has been used as a skin ointment, to promote reproductive fertility, and to alleviate symptoms associated with arthritis. Ashwagandha is comprised of anaferine (alkaloid), anahygrine (alkaloid), beta-sisterol, chlorogenic acid (in leaf only), cysteine (in fruit), cuscohygrine (alkaloid), iron, pseudotropine (alkaloid), scopoletin, somniferinine (alkaloid), somniferiene (alkaloid), tropanol (alkaloid), withanine (alkaloid), withananine (alkaloid) and withanolides A-Y (steroidal lactones).

For the present invention, schizandra berry (*Schisandra Chinensis*) is used as an adaptogenic tonic with liver protecting effects. The berry's primary hepatoprotective (liver protecting) and immuno-modulating constituents are the lignans schizandrin, deoxyschizandrin, gomisins, and pregomisin, which are found in the seeds of the fruit. Further, schizandra is said to nourish the kidneys, astringe the kidneys and stop diarrhea, arrest excessive sweating, provide calming, generate body fluids and alleviate thirst.

Another adaptogen, eleuthero (*Eleutherococcus Senticosus*), is used in the composition to improve stamina and brain chemistry. In addition to being adaptogenic, eleuthero is anticholesteremic, is mildly anti-inflammatory, is antioxidant, is a nervine and an immune tonic. It is useful particularly for hypofunctioning of the endocrine system and adrenal exhaustion. Further, eleuthero is said to improve memory, reduce cortisol levels and reduce inflammation, provide radiological protection, chemo-protection, and be immunogenic. Chemically, eleuthero contains eleutherosides, and triterpenoid saponins which are lipophilic.

Further, in the present invention, goji berry (*Lycium Chinense*) is provided as a high source of vitamin C. Further, goji berry is believed to enhance immune system function, improve eyesight, protect the liver, boost sperm production and improve circulation, among other effects. Further, goji berry acts on the liver, lungs, and kidneys. Also, goji berry may be used to treat inflammation and some types of skin diseases. In modern times, goji berry has been touted as a great source of antioxidants.

In the composition, astragalus (*Astragalus Membranaceus*) is provided as another adaptogenic botanical. Astralagus is used to speed healing and treat diabetes. It is also traditionally used to strengthen the immune system and in the healing of wounds and injuries. Further, astragalus is primarily considered a tonic for enhancing metabolism and digestion. Also, astragalus is used to improve the functioning of the lungs, adrenal glands and the gastrointestinal tract, increase metabolism and sweating, promote healing and reduce fatigue. In addition, astragalus increases the production of interferon and activates immune cells such as macrophages.

For flavoring, sarsaparilla (*Smilax Medicus*—Mexican variety) is included in the composition. In addition to flavor, sarsaparilla is also used for medical benefits. For instance, sarsaparilla has been used to cure syphilis. Also, sarsaparilla was used to improve vigor. Sarsaparilla contains active principles, Parillin (Smilacin), glucoside, sarsapic acid, sarsapogenin (related to progesterone and used in its synthesis), sarsaponin and starch. Also provided for flavor is mangosteen (*Garcinia Mangostana*). In addition to flavor, mangosteen provides a high source of vitamin C and antioxidants. Further, pomegranate fruit (*Punica granatum*) is provided for flavor and as a high source of vitamin C. Pomegranate is also a good source of the B vitamin, pantothenic acid, potassium and antioxidant polyphenols. Research indicates that pomegranate juice may be effective against prostate cancer and osteoarthritis, and may slow the onset or development of prostate cancer. Further, pomegranate may also have antiviral and antibacterial effects against dental plaque.

In the synergistic composition, damiana leaf (*Tumera Diffusa*) is used as a mild sedative to soothe nervousness. Further, damiana leaf is used to treat conditions ranging from coughs to constipation to depression. It is also used to help with energy, emphysema, low estrogen, frigidity, hot flashes, impotency, infertility, menopause, Parkinson's disease, inflammation of the prostate, Lou Gehrig's disease, and diseases and disorders dealing with reproductive organs in both males and females. For additional soothing of nervousness, passion flower (*Passiflora incarnata*) is provided in the composition. Passion flower has been used to treat insomnia, hysteria, and epilepsy, and is also valued for its painkilling properties. Also, passion flower has been found to contain beta-carboline harmala alkaloids which are MAOIs with antidepressant properties. Further, passion flower may be effective for treating anxiety disorders.

For the present invention, green tea (*Camellia sinensis*) is provided for flavor and for its antioxidant properties. In fact, green tea includes high levels of polyphenols and other antioxidants that result in a reduced risk of heart disease and reduced risk of certain types of cancer. Further, green tea has been found to reduce cognitive impairment. Also, it is suggested that green tea prevents obesity as well as rheumatoid arthritis.

In order to improve liver functioning, the composition includes milk thistle (*Carduus Marianus*). Typically, milk thistle has been used to treat liver cirrhosis, chronic hepatitis (liver inflammation), and gallbladder disorders. Also, milk thistle is used to lower cholesterol levels, reduce insulin resistance in people with type 2 diabetes who also have cirrhosis, reduce the growth of cancer cells in breast, cervical, and prostate cancers, and to ameliorate hangovers. The active compound in milk thistle is silymarin, a mixture of at least 4 closely related flavonolignans.

Finally, the composition is completed with white willow bark (*Salix alba*). In the composition, white willow bark is used as an analgesic. In fact, white willow bark has been used since the $5^{th}$ century B.C., to ease aches and pain and to reduce fevers.

While the particular Adaptogenic Tea as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A composition for promoting stress resistance consisting of rhodiola, ashwagandha, schisandra berry, sarsaparilla, goji berry, mangosteen, pomegranate fruit, damiana leaf, passion flower, eleuthero, green tea, astragalus, milk thistle, and white willow bark.

2. A composition as recited in claim 1 wherein the composition is two parts by volume rhodiola, two parts by volume ashwagandha, two parts by volume schisandra berry, two parts by volume sarsaparilla, two parts by volume goji berry, one part by volume mangosteen, one part by volume pomegranate fruit, one part by volume damiana leaf, one part by volume passion flower, one part by volume eleuthero, one part by volume green tea, one part by volume astragalus, one part by volume milk thistle, and one part by volume white willow bark.

3. A composition as recited in claim 1 wherein the composition is brewed into tea.

4. A composition for promoting stress resistance comprising rhodiola, ashwagandha, schizandra berry, eleuthero and astralagus as adaptogens, and damiana leaf and passion flower as sedatives.

5. A composition as recited in claim 4 further comprising milk thistle for promoting liver function.

6. A composition as recited in claim 5 further comprising white willow bark as an analgesiac.

7. A composition as recited in claim 6 further comprising goji berry, mangosteen, and pomegranate fruit for providing vitamin C.

8. A composition as recited in claim 7 further comprising green tea for providing antioxidants.

9. A composition as recited in claim 8 further comprising sarsaparilla for flavoring.

10. A composition as recited in claim 9 wherein the composition is two parts by volume rhodiola, two parts by volume ashwagandha, two parts by volume schisandra berry, two parts by volume sarsaparilla, two parts by volume goji berry, one part by volume mangosteen, one part by volume pomegranate fruit, one part by volume damiana leaf, one part by volume passion flower, one part by volume eleuthero, one part by volume green tea, one part by volume astragalus, one part by volume milk thistle, and one part by volume white willow bark.

11. A composition as recited in claim 10 wherein the composition is brewed into tea.

12. A composition as recited in claim 11 wherein the tea is frozen before consumption.

13. A composition as recited in claim 12 wherein fruit and hibiscus flower are added to the tea before freezing.

14. A composition as recited in claim 12 wherein soy milk, vanilla, cinnamon, virgin coconut oil and lecithin are added to the tea before freezing.

15. A tea for promoting health and reducing stress comprising rhodiola, ashwagandha, schizandra berry, eleuthero and astralagus as adaptogens, damiana leaf and passion flower as sedatives, and milk thistle for promoting liver function.

16. A tea as recited in claim 15 further comprising white willow bark as an analgesiac, and goji berry, mangosteen, and pomegranate fruit for providing vitamin C.

17. A tea as recited in claim 16 further comprising green tea for providing antioxidants and sarsaparilla for flavoring.

18. A tea as recited in claim 17 wherein the composition is two parts by volume rhodiola, two parts by volume ashwagandha, two parts by volume schisandra berry, two parts by volume sarsaparilla, two parts by volume goji berry, one part by volume mangosteen, one part by volume pomegranate fruit, one part by volume damiana leaf, one part by volume passion flower, one part by volume eleuthero, one part by volume green tea, one part by volume astragalus, one part by volume milk thistle, and one part by volume white willow bark.

* * * * *